US011680925B2

United States Patent
Hughes et al.

(10) Patent No.: US 11,680,925 B2
(45) Date of Patent: Jun. 20, 2023

(54) SYSTEMS AND METHODS FOR ELECTROCHEMICAL HEMATOCRIT DETERMINATION BY ALTERNATE CURRENT IMPEDANCE PHASE ANGLE DETERMINATIONS

(71) Applicant: Polymer Technology Systems, Inc., Indianapolis, IN (US)

(72) Inventors: Gary L. Hughes, Anderson, IN (US); Ryan D. Jesswein, Indianapolis, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 224 days.

(21) Appl. No.: 14/952,360

(22) Filed: Nov. 25, 2015

(65) Prior Publication Data
US 2016/0146750 A1    May 26, 2016

Related U.S. Application Data

(60) Provisional application No. 62/084,362, filed on Nov. 25, 2014.

(51) Int. Cl.
*G01N 27/327*    (2006.01)
*G01N 33/49*    (2006.01)
*G01N 15/05*    (2006.01)

(52) U.S. Cl.
CPC ..... *G01N 27/3274* (2013.01); *G01N 27/3271* (2013.01); *G01N 27/3273* (2013.01);
(Continued)

(58) Field of Classification Search
CPC ......... G01N 27/3274; G01N 27/3273; G01N 33/49; G01N 27/3271; G01N 27/3275;
(Continued)

(56) References Cited

U.S. PATENT DOCUMENTS

2004/0157337 A1    8/2004  Burke et al.
2004/0256248 A1*  12/2004  Burke ................ G01N 27/3274
                                                                205/792
(Continued)

FOREIGN PATENT DOCUMENTS

CN            102147390 A      8/2011
CN            103808774 A      5/2014
WO      WO 2013030369 A1 *    3/2013   ......... G01N 27/3274

OTHER PUBLICATIONS

"Frequency Definition of frequency in English by Oxford Disctionaries" http://en.oxforddictionaries.com/definition/frequency.*
(Continued)

*Primary Examiner* — Michael Y Sun
(74) *Attorney, Agent, or Firm* — Haynes and Boone, LLP (57) ABSTRACT

A system for determining a level of hematocrit includes a test strip configured to receive a sample; a meter configured to receive the test strip; and further including circuitry and a microprocessor, the circuitry and microprocessor configured to apply electrical energy to the test strip and the sample and determine an electrical property of the sample, either the impedance phase angle or the impedance magnitude of the test strip and the sample and, based on the electrical property, calculate the level of hematocrit in the sample.

9 Claims, 8 Drawing Sheets

(52) U.S. Cl.
CPC ..... *G01N 27/3275* (2013.01); *G01N 27/3277* (2013.01); *G01N 33/49* (2013.01); *G01N 2015/055* (2013.01); *G01N 2333/904* (2013.01); *G01N 2496/80* (2013.01)

(58) Field of Classification Search
CPC ......... G01N 27/3277; G01N 2015/055; G01N 2333/904; G01N 2496/80
See application file for complete search history.

(56) References Cited

U.S. PATENT DOCUMENTS

| | | |
|---|---|---|
| 2007/0264721 A1 | 11/2007 | Buck |
| 2011/0155590 A1* | 6/2011 | Huffstodt ........... G01N 27/3271 205/792 |
| 2013/0081589 A1 | 4/2013 | Kraf et al. |
| 2013/0084589 A1 | 4/2013 | Kraft et al. |
| 2014/0231273 A1* | 8/2014 | McColl .............. G01N 27/3274 205/792 |

OTHER PUBLICATIONS

International Search Report in co-pending PCT Application No. PCT/US2015/062706 dated Feb. 1, 2016 (3 pages).
Office Action and Search Report dated May 22, 2018 issued in parallel Chinese Patent App. No. 201580074371.7 (12 pages).
Extended European Search Report and Search Opinion dated Jun. 19, 2018 issued in parallel European Patent App. No. 15862237.3 (7 pages).

\* cited by examiner

SYSTEMS AND METHODS FOR ELECTROCHEMICAL HEMATOCRIT DETERMINATION BY ALTERNATE CURRENT IMPEDANCE PHASE ANGLE DETERMINATIONS

CROSS-REFERENCE TO RELATED APPLICATIONS

This Application claims the benefit of Provisional Application No. 62/084,362 filed on Nov. 25, 2014, titled "Electrochemical Hematocrit Determination By Alternate Current Impedance Phase Angle Determinations," the entire disclosure of which is hereby incorporated by reference.

BACKGROUND

Hematocrit is a blood test that measures the percentage of the volume of whole blood that is made up of red blood cells. This measurement depends on the number of red blood cells and the size of red blood cells. The hematocrit (Ht or HcT, British English spelling "haematocrit") also is known as "packed cell volume" (PCV) or "erythrocyte volume fraction" (EVF). It is normally about 45% for men and 40% for women.

In many situations, it is desirable to know the percentage of red blood cells in an individual's blood. Hematocrit levels can indicate excessive bleeding (including internal bleeding), the destruction of red blood cells (due to disease), the decreased production of red blood cells, malnutrition problems, over hydration, dehydration, low availability of oxygen, Erythrocytosis, Cor pulmonale, and other conditions. Hematocrit levels may also affect the results of various blood analyte tests.

BRIEF SUMMARY

In one embodiment, a system for determining a level of hematocrit includes a test strip configured to receive a sample, and a meter configured to receive the test strip; and further including circuitry and a microprocessor, the circuitry and microprocessor configured to apply electrical energy to the test strip and the sample and determine an impedance magnitude and phase angle of the test strip and the sample and, based on the impedance magnitude and phase angle, calculate the level of hematocrit in the sample. Optionally, the circuitry and microprocessor are further configured to determine an impedance magnitude and phase angle of the test strip and the sample. Alternatively, the level of hematocrit is based on both the impedance phase angle and the impedance magnitude. In one configuration, the circuitry and microprocessor are further configured to determine a glucose level of the sample. In another configuration, the level of hematocrit determined is based on the interrelationship between impedance magnitude and phase angle, wherein the glucose level and the level of hematocrit have disparate but proportional impacts on the impedance magnitude and the impedance phase angle, such that the level of each of the glucose level and the level of hematocrit is determinable. Optionally, the test strip includes a first sample window, the first sample window including a first electrode and a second electrode. Alternatively, the glucose level and the level of hematocrit are both determined from the sample in the single sample window. Optionally, the single sample window includes a first set of electrodes and a second set of electrodes. In another configuration, the first set of electrodes is configured to test for impedance magnitude, and the second set of electrodes is configured to test for impedance phase angle. Optionally, the test strip includes a first sample window and a second sample window, the first sample window including electrodes having a reagent for glucose testing.

In one embodiment, a method for determining a level of hematocrit includes providing a system, the system including a test strip configured to receive a sample; a meter configured to receive the test strip and further including circuitry and a microprocessor, the circuitry and microprocessor configured to apply electrical energy to the test strip and the sample and determine an impedance magnitude and phase angle of the test strip. The method further includes receiving a sample at the test strip and inserting the test strip into the meter. The method further includes applying a current to the test strip from the meter. The method further includes determining a phase angle for the sample using the circuitry and microprocessor. The method further includes calculating the level of hematocrit in the sample at the meter and providing an output of the level of hematocrit to a user. Optionally, the method further includes determining, using the circuitry and microprocessor, an impedance of the test strip and the sample. In one configuration, the level of hematocrit is based on both the impedance phase angle and the impedance magnitude. Optionally, the method further includes determining a glucose level of the sample, using the circuitry and microprocessor. Optionally, the level of hematocrit determined is based on the interrelationship between impedance magnitude and phase angle, wherein the glucose level and the level of hematocrit have disparate but proportional impacts on the impedance magnitude and the impedance phase angle, such that the level of each of the glucose level and the level of hematocrit is determinable. Alternatively, the test strip includes a first sample window, the first sample window including a first electrode and a second electrode. In one configuration, the glucose level and the level of hematocrit are both determined from the sample in the single sample window. In another configuration, the single sample window includes a first set of electrodes and a second set of electrodes. Optionally, the first set of electrodes is configured to test for impedance magnitude, and the second set of electrodes is configured to test for impedance phase angle. Alternatively, the test strip includes a first sample window and a second sample window, the first sample window including electrodes having a reagent for glucose testing.

In one embodiment, a system for determining a level of hematocrit includes a test strip configured to receive a sample and a meter configured to receive the test strip. The system further includes circuitry and a microprocessor, the circuitry and microprocessor configured to apply electrical energy to the test strip and the sample and determine one electrical property of the sample, either an impedance phase angle or an impedance magnitude and, based on the at least one electrical property, calculate the level of hematocrit in the sample.

DETAILED DESCRIPTION

Certain terminology is used herein for convenience only and is not to be taken as a limitation on the embodiments of the systems and methods for electrochemical hematocrit determination by alternate current impedance magnitude and phase angle determinations. In the drawings, the same reference letters are employed for designating the same elements throughout the several figures.

Hematocrit usually is measured using a Coulter counter. The output of the Coulter counter is an electronic signal, which signal could be used to automatically adjust the output of the lipid meter. Hematocrit levels may be important to a number of health analyses. The occurrence of hematocrits may affect the detection of glucose, various lipids, and a variety of other analyte detection. Therefore, in many tests, hematocrits are either eliminated or compensated for.

Figure 1:
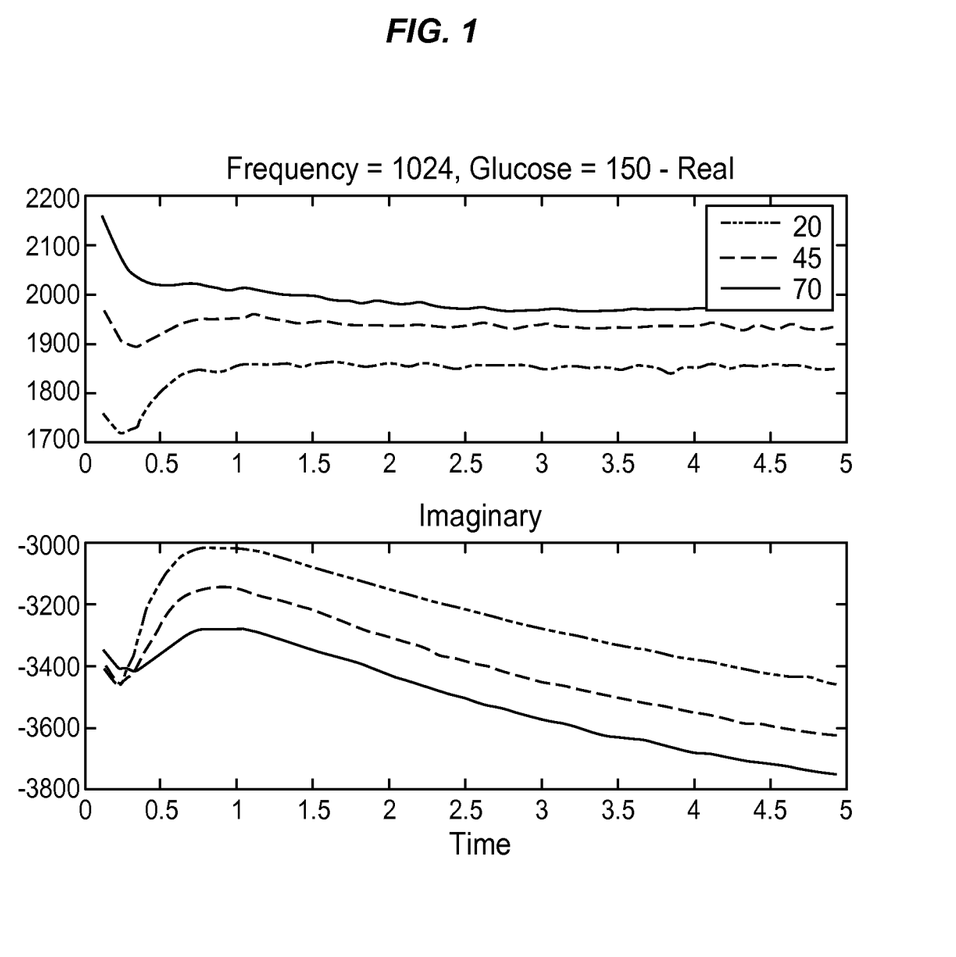
FIG. 1 shows the result of an exemplary test using an electrochemical test strip and meter to test for glucose.

FIG. 1 shows the result of an exemplary test using an electrochemical test strip and meter to test for glucose. The samples provided have different hematocrit levels, so that the effect of hematocrit on glucose can be measured. FIG. 1 shows that, at different hematocrit levels, the same level of glucose generates a different impedance reading. This study was conducted using alternating current. The x-axis is representative of time and the y-axis is representative of impedance. Hematocrit levels of 20%, 45%, and 70% are shown by the various lines.

Figure 2:
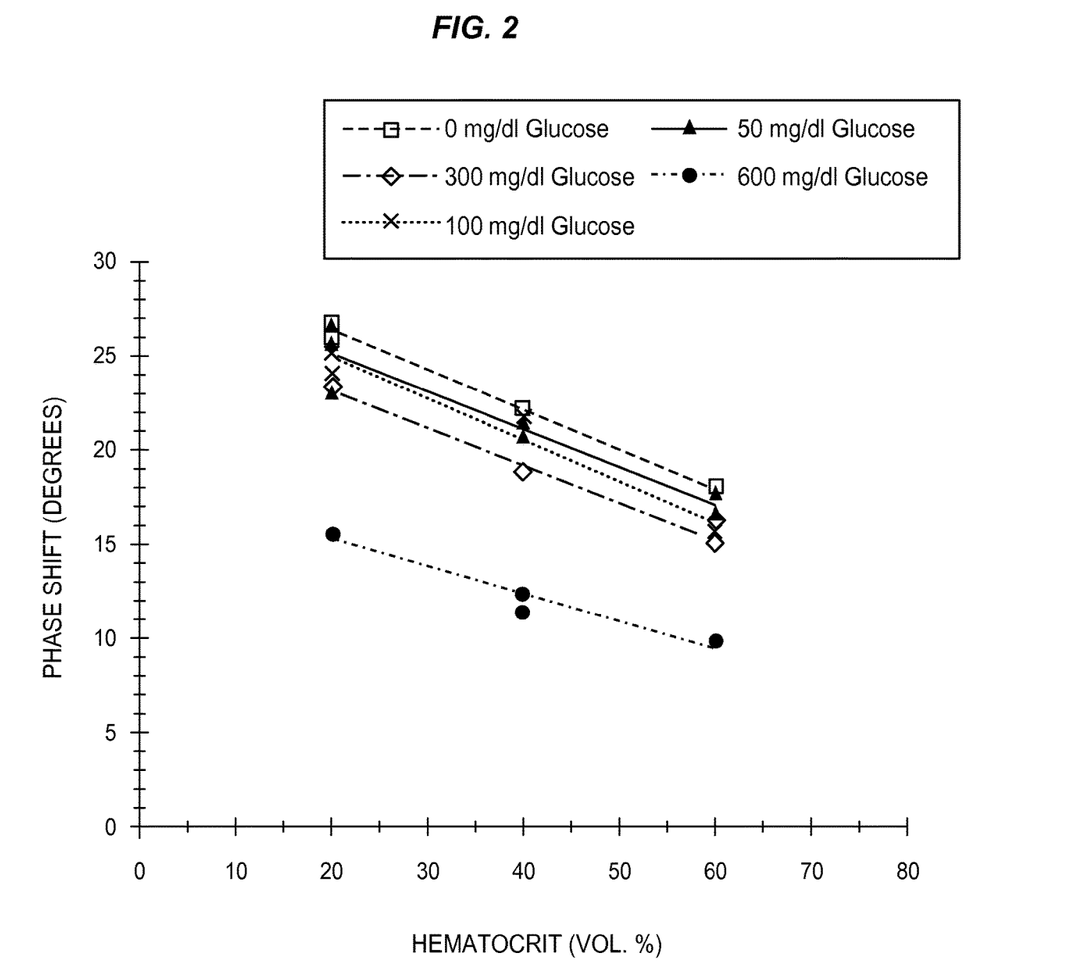
FIG. 2 depicts an exemplary result showing that phase shift is related to the level of hematocrit and glucose.

FIG. 2 shows that phase shift is related to the level of hematocrit and glucose. Therefore, if the level of glucose in a sample is determined, then the level of hematocrit may be determined according to the phase shift. At multiple levels of glucose, an increase in hematocrit results in a decrease in phase shift.

Figure 3:
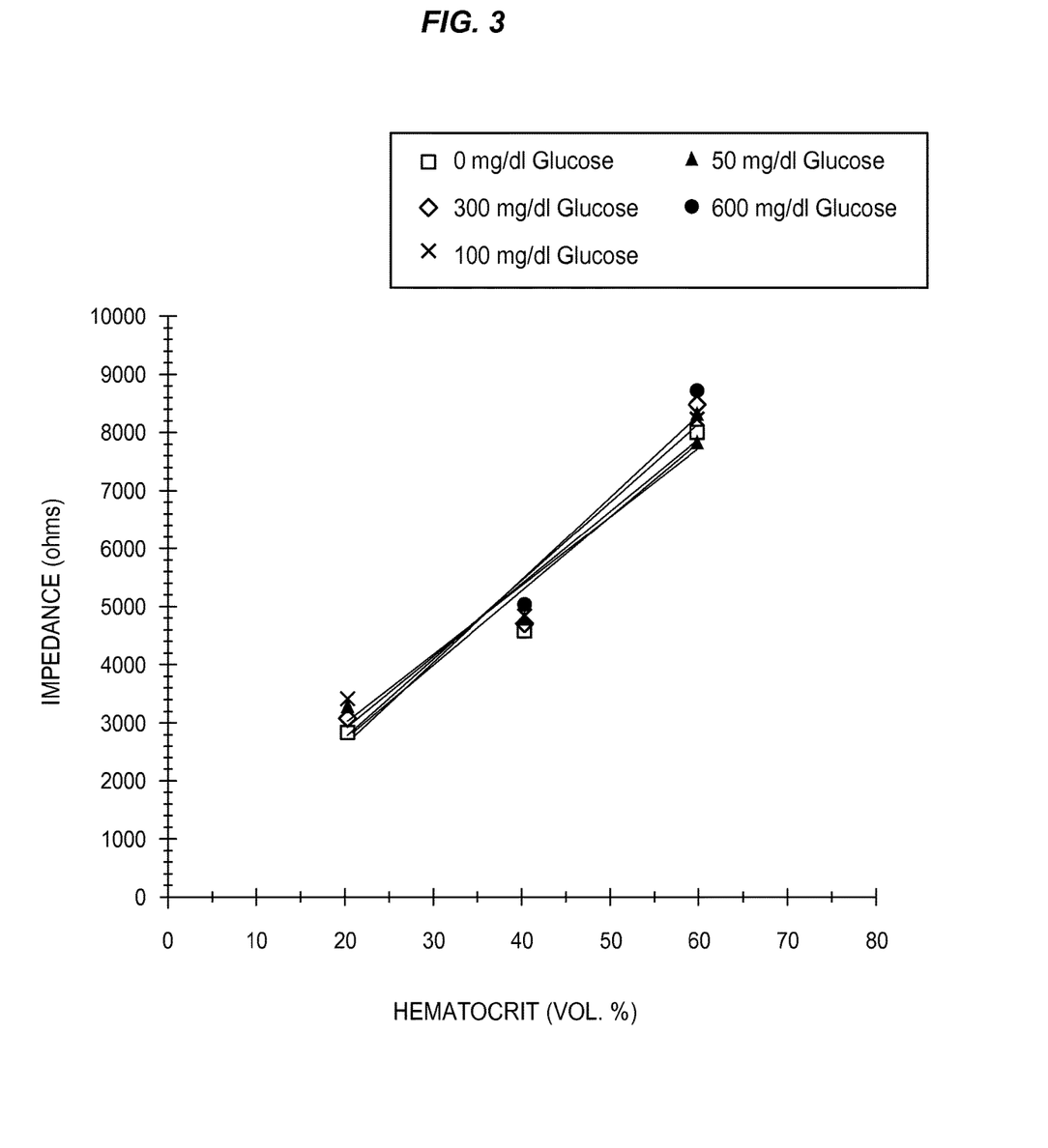
FIG. 3 depicts an exemplary result showing the impedance increase when hematocrit levels are higher for a variety of different glucose levels.

FIG. 3 shows the impedance increase when hematocrit levels are higher for a variety of different glucose levels. Again, this is representative of tests done in a test strip, using an electrochemical meter. An increase in hematocrit results in an increase in measured impedance magnitude.

From these FIGS. 1-3, it can be determined that the hematocrit levels affect the measured impedance and phase angle as it relates to the detection of glucose, and that the phase shift is related to the glucose level and the hematocrit level; however, the phase shift for different levels of glucose has approximately the same slope when the phase shift is compared to the hematocrit level. Therefore, it is possible to determine the hematocrit level based on impedance levels and phase shift levels.

Figure 4:
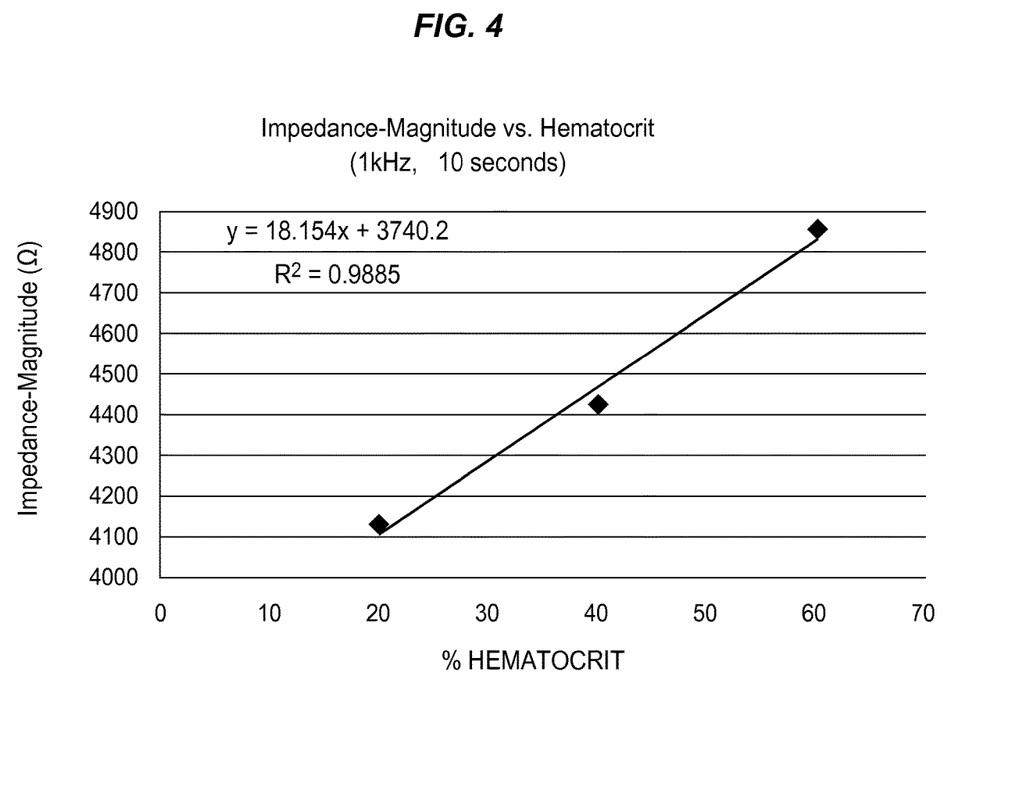
FIG. 4 shows an exemplary conceptual model of how hematocrit changes the magnitude of impedance.

FIG. 4 shows a conceptual model of how hematocrit changes the magnitude of impedance. As shown, the impedance magnitude versus certain percentages of hematocrit for a period of ten seconds. An equation may be determined for the slope based on the data. In this case, the equation is $y=18.154x+3740.2$. This is purely exemplary of a working equation, and numerous other equations may be possible. This graph of Impedance Magnitude vs. Hematocrit duplicates expected and previously observed results.

Figure 5:
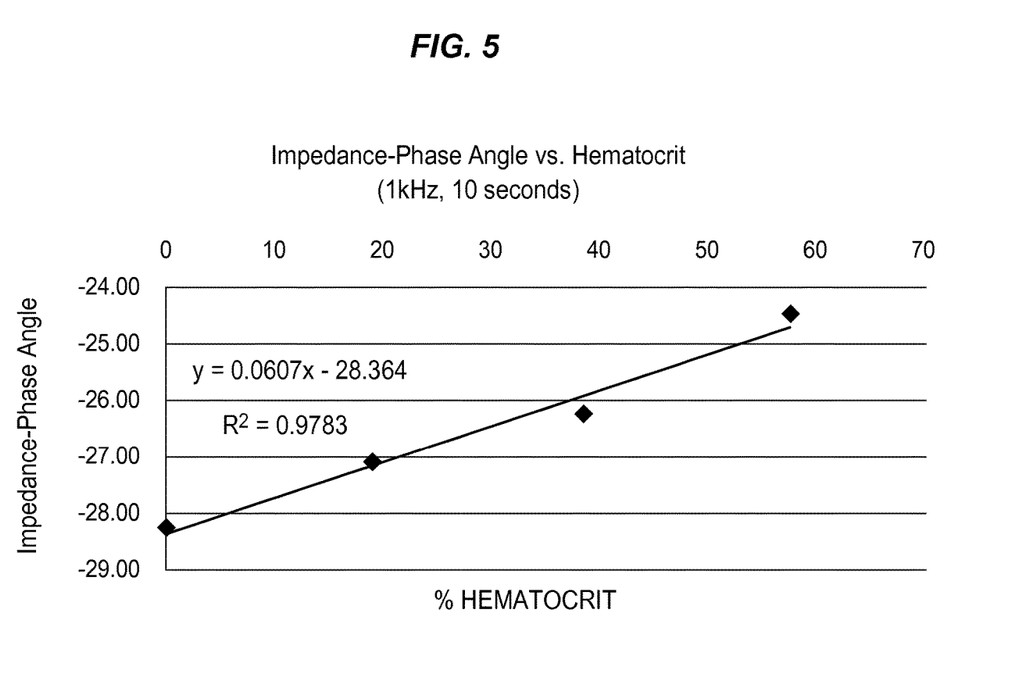
FIG. 5 shows an exemplary conceptual model of how hematocrit changes the impedance phase angle.

FIG. 5 shows a conceptual model of how hematocrit changes the impedance phase angle. As shown, the impedance magnitude versus certain percentages of hematocrit for a period of ten seconds. An equation may be determined for the slope based on the data. In this case, the equation is $y=0.0607x+28.364$. This is purely exemplary of a working equation, and numerous other equations may be possible. This graph of Impedance Phase Angle vs. Hematocrit duplicates expected and previously observed results.

Figure 6:
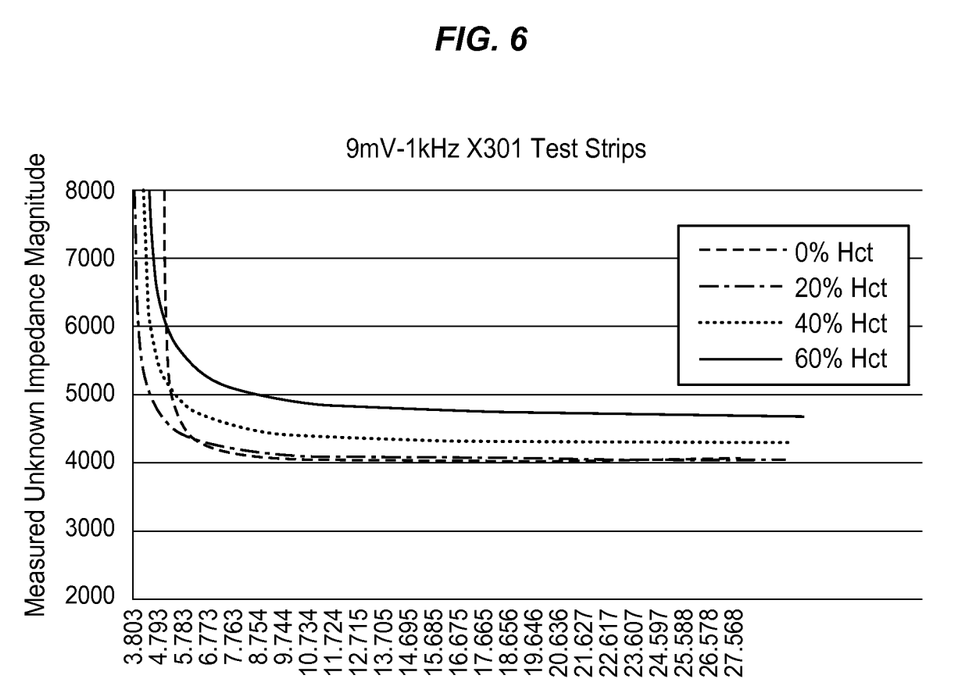
FIG. 6 depicts an exemplary result showing a graph of impedance vs. time for various levels of hematocrit in a 9 mV-1 kHz X301 test strip.

FIG. 6 shows a graph of Impedance vs. Time for various levels of hematocrit in a 9 mV-1 kHz X301 test strip. The hematocrit levels were unknown in these samples; however, the hematocrit levels were able to be determined based on the impedance readings at approximately 5.783 seconds, 7.763 seconds, and 10.734 seconds. The significance of this graph is that it assists in determining the time at which the effects of hematocrit are at constant. In this graph, the y-axis may represent impedance magnitude. As shown, after approximately ten seconds, the effect of hematocrit on impedance has leveled out enough to provide a measureable difference between various hematocrit levels based on the impedance (magnitude and phase angle).

Figure 7:
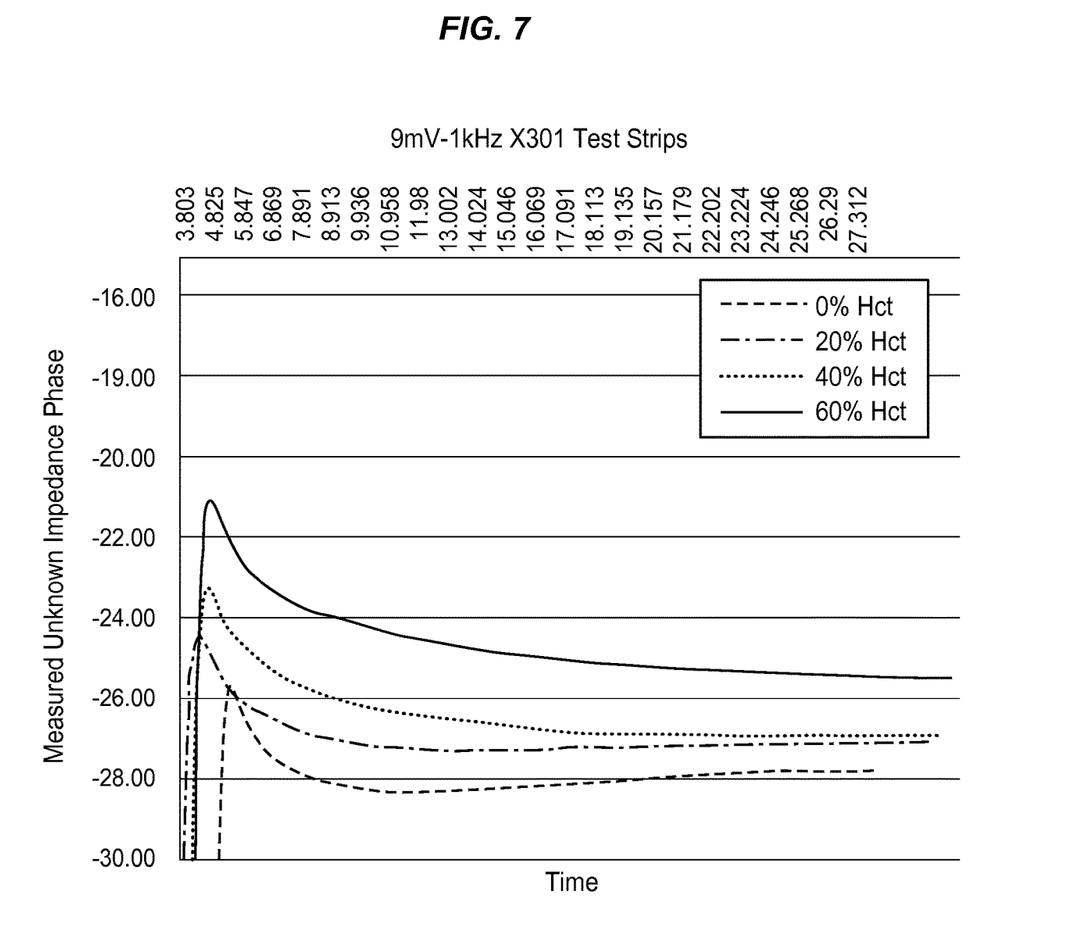
FIG. 7 depicts an exemplary result showing that the phase angle measurements provide for differentiation of the hematocrit levels.

Experimentally, test strips with unknown hematocrit levels were tested to determine if the strips could be differentiated based on the impedance (magnitude and phase angle). As shown in FIG. 7, the phase angle measurements provide for differentiation of the hematocrit levels.

Therefore, multiple setups are possible for a test strip. In one scenario, an electrochemical test strip may be provided with a meter for reading the strip. The electrochemical test strip includes a first electrode and a second electrode for measuring impedance and phase change provided by the sample. The meter is designed to provide current to the strip and monitor the current to determine the impedance and phase change.

In many embodiments, the meter includes an algorithm for correcting for calculating hematocrit. Alternatively, the algorithm may be implemented in various apparatuses. Various embodiments of systems and methods described herein may be implemented fully or partially in software and/or firmware. This software and/or firmware may take the form of instructions contained in or on a non-transitory computer-readable storage medium. Those instructions then may be read and executed by one or more processors to enable performance of the operations described herein. The instructions may be in any suitable form such as, but not limited to, source code, compiled code, interpreted code, executable code, static code, dynamic code, and the like. Such a computer-readable medium may include any tangible non-transitory medium for storing information in a form readable by one or more computers such as, but not limited to, read only memory (ROM); random access memory (RAM); magnetic disk storage media; optical storage media; a flash memory, etc.

Embodiments of systems and methods described herein may be implemented in a variety of systems including, but not limited to, smartphones, tablets, laptops, and combinations of computing devices and cloud computing resources. For instance, portions of the operations may occur in one device, and other operations may occur at a remote location, such as a remote server or servers. For instance, the collection of the data may occur at a smartphone, and the data analysis may occur at a server or in a cloud computing resource. Any single computing device or combination of computing devices may execute the methods described.

A microprocessor in the meter then estimates the hematocrit levels based on an internal equation. In some alternatives, the test strip also may include another testing area with additional electrodes or reactants that produce a reaction with glucose. In some alternatives, the test area for glucose may be the same as the test area for hematocrits. Since the amount of glucose in a sample affects the impedance and phase angle at a different rate than hematocrit, the level of glucose and the level of hematocrit can be determined. In the above configurations, additional testing areas may be included as well. These additional testing areas may test for a wide variety of analytes which may be corrected for hematocrit.

Figure 8:
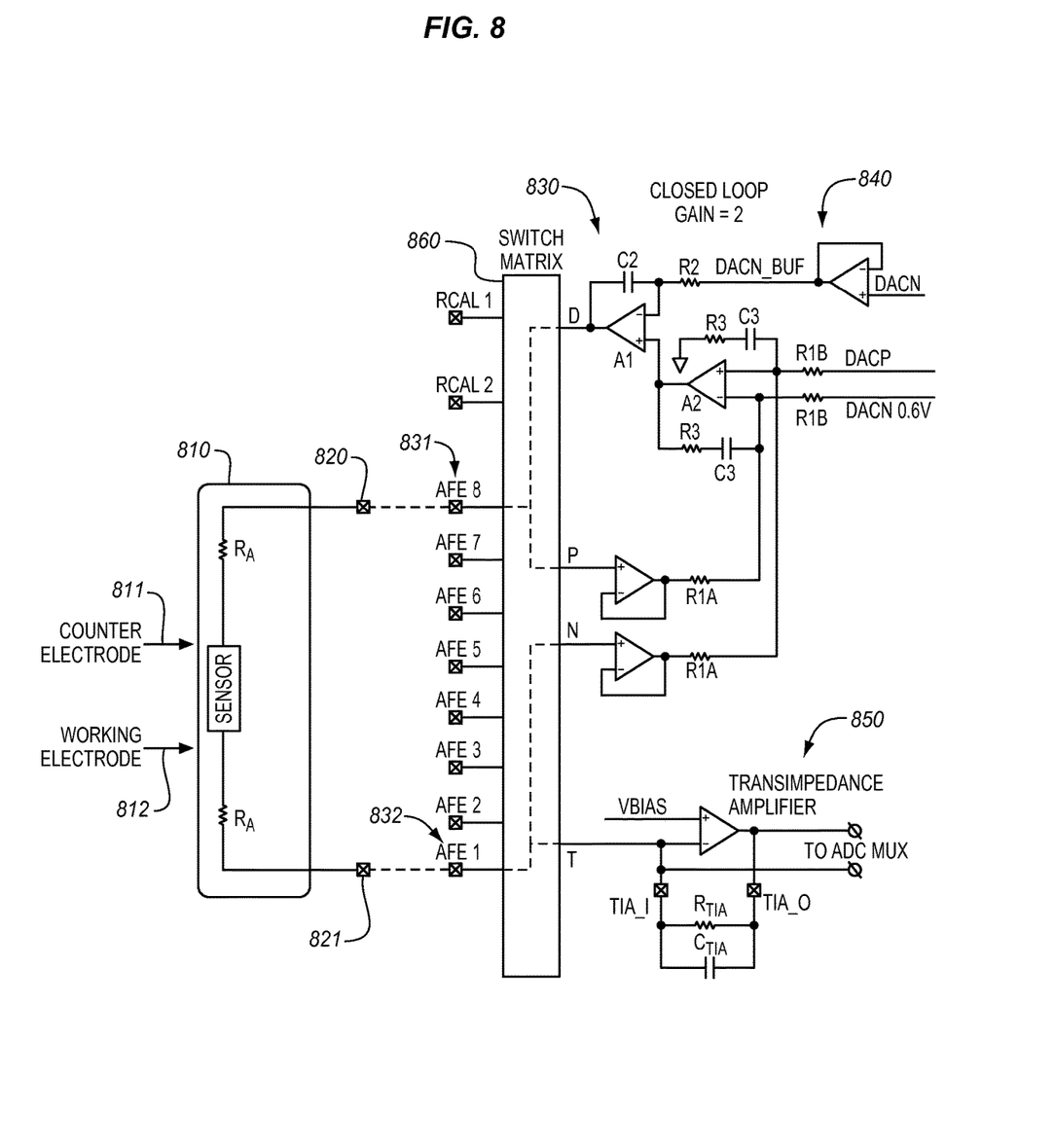
FIG. 8 shows an exemplary structure for a test strip and meter combination.

An exemplary structure for a test strip and meter combination is shown in FIG. 8. Essentially, a test strip 810 is configured with a working electrode 812 and a counter electrode 811. In alternatives, additional electrodes may be included, such as reference electrodes, etc. Test strip 810 also includes connection points 820, 821. Connection points 820, 821 are configured to contact connection points 831, 832 on meter circuitry 830 when the test strip 810 is inserted into the meter. The meter circuitry 830 may include an excitation buffer amplifier loop 840, a transimpedance amplifier 850, and a switch matrix 860. The excitation buffer amplifier loop 840 may provide the needed excitation current to the test strip 810 through switch matrix 860. Generally, the excitation buffer amplifier loop 840 provides the needed current to perform measurements. The transimpedance amplifier 850 is interconnected to a microprocessor and generally receives current through the test strip 810 that includes a sample and provides the signal in a usable form to the microprocessor. The transimpedance amplifier 850 provides current-to-voltage conversion for measurement by the ADC (microprocessor).

The system shown in FIG. 8 is merely exemplary, and numerous alternatives will be available.

In short, the idea is to determine the hematocrit of the sample by taking an AC impedance reading at the beginning, middle, or end of the DC measurement. By determining the magnitude, phase angle, or both, a hematocrit value may be assigned from a predetermined equation. After determining the hematocrit, the concentration may be adjusted mathematically based on the known bias of hematocrit affect.

Red blood cell interference has been identified as a contributor to biased analyte results in the many analyte systems, including those that test for glucose and cholesterol analytes. The ability to determine a hematocrit's influence in analyte measurement on the meter can greatly reduce the analyte's result error. A proprietary microprocessor chip can be used for the detection of the glucose analyte in a whole blood sample via a DC measurement, as well as apply an AC voltage to electrodes. Based on real and imaginary results, a magnitude and phase angle is calculated. System specific factors such as the hematocrit correction factor (whether linear regression parameters or a single coefficient), the time scale of the AC and DC voltage applications, and the use of phase angle and/or magnitude results dictate a "corrected" glucose value based on the DC measurement.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for determining a level of hematocrit, comprising:
a test strip configured to receive a sample;
a meter configured to receive the test strip; and
further including circuitry and a microprocessor, the circuitry and the microprocessor configured to apply electrical energy to the test strip, the test strip having a working electrode and a counter electrode, and the sample and determine an impedance phase angle of the test strip and the sample and the circuitry and the microprocessor are further configured to determine an impedance magnitude of the test strip and, the circuitry and the microprocessor applying a direct current, to the working electrode and the counter electrode, through a switch matrix, to determine the impendence magnitude and an alternating current, to the working electrode and the counter electrode, through the switch matrix, to determine the impedance phase angle, based on the impedance phase angle and the impedance magnitude, calculate the level of hematocrit, the microprocessor determining the level of hematocrit based on an amount of glucose in the sample that affects the impedance magnitude and the impedance phase angle at a different rate than the level of hematocrit, a level of glucose and the level of hematocrit.

2. The system of claim 1, wherein the circuitry and the microprocessor are further configured to determine a glucose level of the sample.

3. The system of claim 2, wherein the level of hematocrit determined is based on the interrelationship between the impedance magnitude and the impedence phase angle, wherein the glucose level and the level of hematocrit have disparate but proportional impacts on the impedance magnitude and the impedance phase angle, such that a level of each of the glucose level and the level of hematocrit is determinable.

4. The system of claim 3, wherein the test strip includes a first sample window, the first sample window including a first electrode and a second electrode.

5. The system of claim 4, wherein the glucose level and the level of hematocrit both are determined from the sample in the single sample window.

6. The system of claim 5, wherein the single sample window includes a first set of electrodes and a second set of electrodes.

7. The system of claim 6, wherein the first set of electrodes is configured to test for the impedance magnitude and the second set of electrodes is configured to test for the impedance phase angle.

8. The system of claim 4, wherein the test strip includes a first sample window and a second sample window, the first sample window including electrodes having a reagent for glucose testing.

9. A system for determining a level of hematocrit, comprising:
a test strip configured to receive a sample;
a meter configured to receive the test strip; and
further including circuitry and microprocessor, the circuitry and the microprocessor configured to apply electrical energy to the test strip, a working electrode and a counter electrode, the circuitry and the microprocessor applying a direct current, to the working electrode and the counter electrode, through a switch matrix, to determine the impendence magnitude and an alternating current, to the working electrode and the counter electrode, through the switch matrix, to determine the impedance phase angle, and, based on the impedance phase angle and the impedance magnitude, calculate the level of hematocrit, determine a level of hematocrit based on an amount of glucose in the sample that affects the impedance magnitude and the impedance phase angle at a different rate than the level of hematocrit, a level of glucose and the level of hematocrit.

\* \* \* \* \*